United States Patent [19]
Hondo et al.

[11] Patent Number: 5,882,669
[45] Date of Patent: Mar. 16, 1999

[54] STARCH COMPOSITIONS AND METHOD FOR CONTROLLING PESTS

[75] Inventors: Masaru Hondo, Osaka; Mutsuo Oi, Hyogo, both of Japan

[73] Assignee: Sumitomo Chemical Company, Limited, Osaka, Japan

[21] Appl. No.: 644,358

[22] Filed: May 10, 1996

[51] Int. Cl.$^6$ ..................................................... A01N 25/12
[52] U.S. Cl. .......................... 424/408; 424/405; 536/102
[58] Field of Search ................................... 424/408, 405; 536/102

[56] References Cited

U.S. PATENT DOCUMENTS

| | | | |
|---|---|---|---|
| 2,547,724 | 4/1951 | Sundholm | 167/33 |
| 4,227,911 | 10/1980 | Leonard et al. | 71/77 |
| 5,180,587 | 1/1993 | Moore | 424/408 |
| 5,516,520 | 5/1996 | Yang et al. | 424/408 |
| 5,536,746 | 7/1996 | Deckeyser et al. | 514/468 |
| 5,567,429 | 10/1996 | Senbo | 424/405 |

FOREIGN PATENT DOCUMENTS

| | | |
|---|---|---|
| 58-109402 | 6/1983 | Japan . |
| 58-109403 | 6/1993 | Japan . |
| 7-33608 | 2/1995 | Japan . |
| 7-126105 | 5/1995 | Japan . |

OTHER PUBLICATIONS

H.E. Aller et al., "Acaricidal Activity of Cellulose Polymers", *Journal of Economic Entomology*, vol. 54, No. 3, Jun. 1961, pp. 511–513.

*Primary Examiner*—Neil S. Levy
*Attorney, Agent, or Firm*—Sughrue, Mion, Zinn, Macpeak & Seas, PLLC

[57] ABSTRACT

The present invention provides a composition for controlling pests, comprising a pregelatinized starch and at least one surfactant selected from a group consisting of dialkyl sulfosuccinate type surfactant, silicone type surfactant and acetylene glycol type surfactant and, if necessary, a carrier such as mineral carrier, a surfactant other than above-mentioned surfactant, a plasticizer and other auxiliary agents. The present invention also provide a method for controlling pests, which comprises treating with the above composition.

According to the present invention, various pests can be effectively controlled. Also, in the agricultural/horticultural field, pests can be controlled without causing a phytotoxicity of crops.

11 Claims, No Drawings

STARCH COMPOSITIONS AND METHOD FOR CONTROLLING PESTS

FIELD OF THE INVENTION

The present invention relates to a composition and a method for controlling pests. More particularly, it relates to a composition for controlling pests, comprising a pregelatinized starch and a kind of surfactant, and a method for controlling pests, which comprises treating with the composition.

BACKGROUND OF THE INVENTION

As one of the methods for controlling pests, a method for capturing or exterminating pests comprising physically sticking them to an adhesive substance is known. For example, a method for killing a fly comprising sticking it to an adhesive ribbon produced by applying an adhesive on a substrate is known. A similar method for cockroaches, long-horned beetles are also known. In Japanese Patent Kokoku No. 59-23352, a method comprising forming an adhesive foam with an adhesive-organic solvent-liquefied petroleum gas and capturing a cockroach using the adhesive foam is described. In Japanese Patent Kokai (Laid-Open) No. 52-105217, a formulation for capturing rodent animals prepared by adding a thickener to a polybutene compound is described. In Japanese Patent Kokai (Laid-Open) No. 4-66502, an aerosol type adhesive composition for capturing pests (e.g. cockroach, mouse, etc.) comprising a polybutene emulsion is described.

The mode of action of these types of composition is mainly capturing pests on the compositions. Therefore, they contain a strong adhesive substance. In these cases, organic solvents are indispensable. However, these auxiliaries often caused severe phytotoxicity to plants to which the compositions were applied. Moreover, these physical pest control methods have the possibility to cause severe crop residue of adhesives and organic solvents. Therefore, a more sophisticated composition useful for physical pest control is required.

Under these circumstances, the present inventors have studied intensively to find a better composition and method for physically controlling pests. As a result, it has been discovered that a composition comprising a pregelatinized starch and a kind of a surfactant is effective for controlling pests and is extremely useful as an agricultural/horticultural agent for controlling pests.

OBJECTS OF THE INVENTION

One object of the present invention is to provide a composition for controlling pests which can effectively control various pests.

Another object of the present invention is to provide a method for controlling pests which comprises using the composition for controlling pests.

These objects as well as other objects and advantages of the present invention will become apparent to those skilled in the art from the following description.

SUMMARY OF THE INVENTION

The present invention provides the following compositions and control method.

(1) A composition for controlling pests, comprising a pregelatinized starch and at least one surfactant selected from the group consisting of dialkyl sulfosuccinate type surfactants, silicone type surfactants and acetylene glycol type surfactants, (2) A composition for controlling pests, comprising a pregelatinized starch, at least one surfactant selected from the group consisting of dialkyl sulfosuccinate type surfactants, silicone type surfactants and acetylene glycol type surfactents, and a propylene glycol, (3) A method for controlling pests which comprises applying a pesticidally effective amount of the composition of the present invention to pests or plants in which pests live.

DETAILED DESCRIPTION OF THE INVENTION

The composition and control method of the present invention can be used for controlling pests, for example, small noxious insects such as Tetranychidae (spider mites) such as *Panonychus citri*, *Tetranychus uriticae* and *Tetranychus kanzawai*, *Aculops pelekassi*, Thysanoptera (thrips), and Aphididea (aphids) such as *Aphis gossypii* Glover and *Myzus persicae* of fruit trees (e.g. citrus, apple, pear, peach, etc.); *Tetranychus kanzawai*, Thysanoptera (thrips), and Aphididea (aphids) of tea; Tetranychidae (spider mites), Aphididea (aphids), Thysanoptera (thrips), *Trialourodes vaporariorum*, and *Bemisia tabaci* of vegetables (e.g. eggplant, tomato, cucumber, pimento, etc.); Tetranychidae (spider mites), Aphididea (aphids), Thysanoptera (thrips), *Trialourodes vaporariorum*, and *Bemisia tabaci* of flowering plants (e.g. carnation, rose, chrysanthemum, babies' breath, poinsettia, etc.); and pathogenic fungi of powdery mildew of various crops.

It is considered that the mode of action of the composition of the present invention is essentially due to physical action. In other words, by applying the composition of the present invention to the above pests, the composition sticks to the pests to either indispose them for behavior or drastically limit the behavior. Thereby, pests are starved to death or are prey for other insects and animals, or are suffocated by covering the respiratory system with the composition.

Examples of the pregelatinized starch include starch obtained by α-isomerizing starch that is obtained from raw materials such as potatoes, sweet potatoes, wheat, corn, tapioca, sago, rice, etc. When using starch from corn of the waxy corn species and tapioca as the raw materials, high control effect is obtained.

Also, β-starch may be used as a formulation material if β-starch is heated to be changed into pregelatinized starch when formulated.

Examples of the surfactant include dialkylsulfo-succinate type surfactant (e.g. Aerol CT-1 manufactured by Toho Kagaku Kogyo Co., Ltd., Neocol YSK manufactured by Daiichi Kogyo Seiyaku Co., Ltd., etc.), silicone type surfactant (e.g. NUC SILICONE, L-77 manufactured by Nihon Yunicar Co., Ltd., KF-618 manufactured by Shinetsu Kagaku Co., Ltd., etc.), acetylene glycol type surfactant (e.g. Sarfinol 104 manufactured by Nisshin Kagaku Co., Ltd., etc.). Among them, a silicone type surfactant is preferred.

Regarding the composition of the present invention, a pregelatinized starch and at least one surfactant selected from the group consisting of dialkyl sulfosuccinate type surfactants, silicone type surfactants and acetylene glycol type surfactant and water and, if necessary, a surfactant other than above-mentioned surfactants, a plasticizer and other auxiliary agents are mixed to form a liquid formulation. Then the liquid formulation is used as it is or after diluting with water so that the resulting solution has a suitable concentration. Otherwise, a pregelatinized starch and at least one surfactant selected from the group consisting of dialkyl sulfosuccinate type surfactants, silicone type surfactants and acetylene glycol type surfactants and, if necessary, a carrier such as a mineral carrier, a surfactant other than the surfactant selected from the group consisting of dialkyl sulfosuccinate type surfactants, silicone type surfactants and acetylene glycol type surfactant, a plasticizer, a water soluble carrier and other auxiliary agents are mixed to form a water-soluble powder or wettable powder, and then the powder is used after dissolving it in water and diluting it with water.

The plasticizer is not necessarily required, but it is preferred to add it to improve physicochemical properties such as plasticity, low-temperature resistance to prevent freezing, etc. Examples thereof include one or more sorts of solvents selected from solvents such as glycerin, polyethylene glycol, ethylene glycol, polypropylene glycol, propylene glycol, etc. Among them, propylene glycol is preferred.

Examples of those which can be used as the mineral carrier include pagodite, talc, kaolin, sodium carbonate, bentonite, silica powder, hydrated silicone dioxide, acid clay, diatomaceous earth powder, pumice powder, etc. Those having a particle size of not more than 45 μm are preferred.

In addition, water-soluble carriers such as urea, boric acid, citric acid, glucose, potassium sorbate, fumaric acid, meleic acid, etc. can also be used as the extender.

It is also possible to mix an antiblastic and antifungal agent, potency enhancing agent, colorant, etc. as the auxiliary agent. It is also possible to prepare the composition by mixing it with insecticide, fungicide, acaricide, plant growth regulator, etc.

The composition of the present invention can be prepared, for example, by charging water in a mixing tank, adding materials such as pregelatinized starch, surfactant, plasticizer, etc. with stirring, followed by stirring uniformly. They may optionally be mixed with heating at 30° to 90° C. Also, if β-starch is used as the formulation material, the formulation is heated so that β-starch is changed into pregelatinized starch when formulated.

The amount of the pregelatinized starch contained in the composition is from 1.5 to 10% by weight in the case of the liquid formulation. In the case of the water-soluble powder and wettable powder, the amount of the pregelatinized starch is from 0.5 to 90% by weight, preferably from 1 to 80% by weight. The amount of the surfactant selected from the group consisting of dialkyl sulfosuccinate type surfactants, silicone type surfactants and acetylene glycol type surfactants is from 1 to 8% by weight. When the plasticizer is mixed, the amount of the plasticizer contained in the formulation is from 5 to 20% by weight.

In the wettable powder, the amount of the mineral carrier is from 10 to 90% by weight, preferably from 20 to 50% by weight.

The composition of the present invention is normally applied after diluting it with water. The application concentration varies depending on the type of pests, the stage and weather conditions, but the dilute solution has a viscosity at which adhesion properties capable of physically exterminating pests can be maintained and the dilute solution can be applied using a sprayer. The concentration of the pregelatinized starch is from 100 to 10000 ppm, preferably from 100 to 3000 ppm.

As the application method of the composition of the present invention, there is a method comprising spraying the composition of the present invention over the pests, biotope of pests and/or plants, using a sprayer such as a power sprayer, a hanging type sprayer, a hand sprayer, etc.

The composition of the present invention can also be used in the agricultural field after mixing it with fertilizer, insecticide, fungicide, acaricide, plant growth regulator, etc.

In the composition and control method of the present invention, pregelatinized starch is used. Therefore, the composition of the present invention does not have a strong adhesive action like a conventional synthetic rubber adhesive. When dry and fine weather lasts for a long period, the composition of the present invention is dried and is scattered as powder, or falls from the surface of the plant together with pests captured. When it rains continuously for a long period, it is washed away by rainwater. Accordingly, the composition of the present invention does not cover the stomata of the plant and cause death, and it does not remain on the crop for a long period. Since the composition of the present invention does not contain an organic solvent that is noxious to the plant, the composition does not damage the surface of the plant and does not exert a noxious influence on the growth. On the other hand, when the composition of the present invention sticks to the body surface of pests having a body length of about several millimeters, it has the effect of limiting the behavior of the pests. Therefore, a direct capturing effect and a respiratory system occlusion effect can be expected. Since the composition of the present invention essentially control pests due to a physical action, problems such as chemical resistance does not arise.

The following Formulation Examples and Test Examples further illustrate the present invention in detail but are not construed to limit the scope thereof.

First, Formulation Examples will be shown. In the Formulation Examples, all "parts" are by weight unless otherwise stated.

FORMULATION EXAMPLE 1

To 79.8 parts of water were added 5.0 parts of pregelatinized starch (Matsunorin M-22, manufactured by Matsutani Kagaku Kogyo Co., Ltd.) and 10.0 parts of propylene glycol (manufactured by Wako Junyaku Co., Ltd.), followed by stirring. Furthermore, 5.0 parts of dialkyl sulfosuccinate (Aerol CT-1, manufactured by Toho Kagaku Kogyo Co., Ltd.) and 0.2 part of antiblastic and antifungal agent (Proxel GXL, manufactured by I.C.I. Japan Co., Ltd.) were added and the mixture was sufficiently stirred to obtain a liquid formulation.

FORMULATION EXAMPLE 2

To 79.8 parts of water were added 5.0 parts of pregelatinized starch (Amicol W, manufactured by Nichiden Kagaku Co., Ltd.) and 10.0 parts of propylene glycol (manufactured by Wako Junyaku Co., Ltd.), followed by stirring. Furthermore, 5.0 parts of dialkyl sulfosuccinate (Aerol CT-1, manufactured by Toho Kagaku Kogyo Co., Ltd.) and 0.2 part of antiblastic and antifungal agent (Proxel GXL, manufactured by I.C.I. Japan Co., Ltd.) were added and the mixture was sufficiently stirred to obtain a liquid formulation.

FORMULATION EXAMPLE 3

To 57.8 parts of water were added 5.0 parts of pregelatinized starch (Matsunorin M-22, manufactured by Matsutani Kagaku Kogyo Co., Ltd.), 25.0 parts of lignin sulfonate (San X P201, manufactured by Sanyo Kokusaku Pulp Co., Ltd.) and 10.0 parts of propylene glycol (manufactured by Wako Junyaku Co., Ltd.), followed by stirring. Furthermore, 2.0 parts of a silicone type surfactant (NUC SILICONE L-77, manufactured by Nihon Yunicar Co., Ltd.) and 0.2 part of antiblastic and antifungal agent (Proxel GXL, manufactured by I.C.I. Japan Co., Ltd.) were added and the mixture was sufficiently stirred to obtain a liquid formulation.

FORMULATION EXAMPLE 4

To 54.8 parts of water were added 5.0 parts of pregelatinized starch (Matsunorin M-22, manufactured by Matsutani Kagaku Kogyo Co., Ltd.), 25.0 parts of lignin sulfonate (San X P201, manufactured by Sanyo Kokusaku Pulp Co., Ltd.) and 10.0 parts of propylene glycol (manufactured by Wako Junyaku Co., Ltd.), followed by stirring. Furthermore, 5.0 parts of dialkyl sulfosuccinate (Aerol CT-1, manufactured by Toho Kagaku Kogyo Co., Ltd.) and 0.2 part of antiblastic and antifungal agent (Proxel GXL, manufactured by I.C.I. Japan Co., Ltd.) were added and the mixture was sufficiently stirred to obtain a liquid formulation.

FORMULATION EXAMPLE 5

To 72.8 parts of water were added 5.0 parts of pregelatinized starch (Amicol W, manufactured by Nichiden Kagaku Co., Ltd.), 10.0 parts of sodium polyphosphate (manufactured by Taihei Kagaku Sangyo Co., Ltd.) and 10.0 parts of ethylene glycol (manufactured by Wako Junyaku Co., Ltd.), followed by stirring. Furthermore, 2.0 parts of a silicone type surfactant (KF-618, manufactured by Shinetsu Kagaku Co., Ltd.) and 0.2 parts of antiblastic and antifungal agent (Proxel GXL, manufactured by I.C.I. Japan Co., Ltd.) were added and the mixture was sufficiently stirred to obtain a liquid formulation.

FORMULATION EXAMPLE 6

To 80.8 parts of water were added 6.0 parts of pregelatinized starch (Matsunorin M-22, manufactured by Matsutani Kagaku Kogyo Co., Ltd.) and 10.0 parts of propylene glycol (manufactured by Wako Junyaku Co., Ltd.), followed by stirring. Furthermore, 3.0 parts of a silicone type surfactant (NUC SILICONE L-77, manufactured by Nihon Yunicar Co., Ltd.) and 0.2 part of antiblastic and antifungal agent (Proxel GXL, manufactured by I.C.I. Japan Co., Ltd.) were added and the mixture was sufficiently stirred to obtain a liquid formulation.

FORMULATION EXAMPLE 7

To 81.8 parts of water were added 6.0 parts of pregelatinized starch (Amicol W, manufactured by Nichiden Kagaku Co., Ltd.) and 10.0 parts of propylene glycol (manufactured by Wako Junyaku Co., Ltd.), followed by stirring. Furthermore, 2.0 parts of a silicone type surfactant (KF-618, manufactured by Shinetsu Kagaku Co., Ltd.) and 0.2 part of antiblastic and antifungal agent (Proxel GXL, manufactured by I.C.I. Japan Co., Ltd.) were added and the mixture was sufficiently stirred to obtain a liquid formulation.

FORMULATION EXAMPLE 8

To 80.8 parts of water were added 3.0 parts of pregelatinized starch (Matsunorin M-22, manufactured by Matsutani Kagaku Kogyo Co., Ltd.) and 10.0 parts of propylene glycol (manufactured by Wako Junyaku Co., Ltd.), followed by stirring. Furthermore, 6.0 parts of silicone type surfactant (NUC SILICONE L-77, manufactured by Nihon Yunicar Co., Ltd.) and 0.2 part of antiblastic and antifungal agent (Proxel GXL, manufactured by I.C.I. Japan Co., Ltd.) were added and the mixture was sufficiently stirred to obtain a liquid formulation.

FORMULATION EXAMPLE 9

To 80.8 parts of water were added 6.0 parts of pregelatinized starch (Matsunorin M-22, manufactured by Matsutani Kagaku Kogyo Co., Ltd.) and 10.0 parts of propylene glycol (manufactured by Wako Junyaku Co., Ltd.), followed by stirring. Furthermore, 3.0 parts of silicone type surfactant (NUC SILICONE L-77, manufactured by Nihon Yunicar Co., Ltd.) and 0.2 part of antiblastic and antifungal agent (Proxel GXL, manufactured by I.C.I. Japan Co., Ltd.) were added and the mixture was sufficiently stirred to obtain a liquid formulation.

FORMULATION EXAMPLE 10

To 82.3 parts of water were added 6.0 parts of pregelatinized starch (Matsunorin M-22, manufactured by Matsutani Kagaku Kogyo Co., Ltd.) and 10.0 parts of propylene glycol (manufactured by Wako Junyaku Co., Ltd.), followed by stirring. Furthermore, 1.5 parts of silicone type surfactant (NUC SILICONE L-77, manufactured by Nihon Yunicar Co., Ltd.) and 0.2 part of antiblastic and antifungal agent (Proxel GXL, manufactured by I.C.I. Japan Co., Ltd.) were added and the mixture was sufficiently stirred to obtain a liquid formulation.

FORMULATION EXAMPLE 11

To 77.8 parts of water were added 6.0 parts of pregelatinized starch (Matsunorin M-22, manufactured by Matsutani Kagaku Kogyo Co., Ltd.) and 10.0 parts of propylene glycol (manufactured by Wako Junyaku Co., Ltd.), followed by stirring. Furthermore, 6.0 parts of silicone type surfactant (NUC SILICONE L-77, manufactured by Nihon Yunicar Co., Ltd.) and 0.2 part of antiblastic and antifungal agent (Proxel GXL, manufactured by I.C.I. Japan Co., Ltd.) were added and the mixture was sufficiently stirred to obtain a liquid formulation.

FORMULATION EXAMPLE 12

To 85.3 parts of water were added 1.5 parts of pregelatinized starch (Matsunorin M-22, manufactured by Matsutani Kagaku Kogyo Co., Ltd.) and 10.0 parts of propylene glycol (manufactured by Wako Junyaku Co., Ltd.), followed by stirring. Furthermore, 3.0 parts of silicone type surfactant (NUC SILICONE L-77, manufactured by Nihon Yunicar Co., Ltd.) and 0.2 parts of antiblastic and antifungal agent (Proxel GXL, manufactured by I.C.I. Japan Co., Ltd.) were added and the mixture was sufficiently stirred to obtain a liquid formulation.

FORMULATION EXAMPLE 13

25.0 Parts of pregelatinized starch (Matsunorin M-22, manufactured by Matsutani Kagaku Kogyo Co., Ltd.), 40.0 parts of lignin sulfonate (San X P201, manufactured by Sanyo Kokusaku Pulp Co., Ltd.), 30.0 parts of citric acid (manufactured by Wako Junyaku Kogyo Co., Ltd.) 3.0 parts of a dialkyl sulfosuccinate type surfactant (Aerol CT-1, manufactured by Toho Kagaku Kogyo Co., Ltd,.) and 2.0 parts of a silicone type surfactant (NUC SILICONE L-77, manufactured by Nihon Yunicar Co., Ltd.) were uniformly pulverized and mixed to obtain water-soluble powder.

FORMULATION EXAMPLE 14

15.0 Parts of pregelatinized starch (Amicol W, manufactured by Nichiden Kagaku Co., Ltd.), 50.0 parts of lignin sulfonate (San X P201, manufactured by Sanyo Kokusaku Pulp Co., Ltd.), 30.0 parts of glucose and 5.0 parts of a silicone type surfactant (NUC SILICONE L-77, manufactured by Nihon Yunicar Co., Ltd.) were uniformly pulverized and mixed to obtain water-soluble powder.

COMPARATIVE FORMULATION EXAMPLE 1

To 80.8 parts of water were added 6.0 parts of β-starch (starch obtained from potatoes) and 10.0 parts of propylene glycol (manufactured by Wako Junyaku Co., Ltd.), followed by stirring. Furthermore, 3.0 parts of silicone type surfactent (NUC SILICONE L-77, manufactured by Nihon Yunicar Co., Ltd.) and 0.2 part of antiblastic and antifungal agent (Proxel GXL, manufactured by I.C.I. Japan Co., Ltd.) were added and the mixture was sufficiently stirred to obtain a liquid formulation.

The following Test Examples illustrate that the composition of the present invention is useful.

Test Example 1

Acaricidal effect test against *Tetranychus uriticae* of bean

A stub of bean (no cane) was planted in a plastic pot having a diameter of 7 cm and a height of 10 cm, and then *Tetranychus uriticae* was inoculated and sufficiently multiplicated. Dilute solutions (dilution ratio: 100) of the compositions of the present invention shown in Formulation Examples 2, 3, 4, 6 and 7 as well as dilute solution (dilution ratio: 100) of an emulsifiable concentrate containing mineral oil as an active ingredient having the physical pesticidal effect as that of the composition of the present invention (Summer Machine 97, manufactured by Agros Co., Ltd.) as a control were sprayed in a sufficient amount over bean, using a hand sprayer. The number of female adults of *Tetranychus uriticae* which were parasitic on bean was examined before spraying and 3 days, 7 days and 15 days after spraying (one field/one pot/three times). The control value was calculated from the following equation. The results are shown in Table 1. The composition of the present invention showed high acaricidal effect which is about the same as that of the emulsifiable concentrate as the control. In this test example, a phytotoxicity wherein leaves of bean are partially dead in the field where the emulsifiable concentrate containing mineral oil as an active ingredient was sprayed. However, no phytotoxicity was recognized in the field of the composition of the present invention.

$$\text{Control value} = \left(1 - \frac{C_b \times \sum_{i=1}^{n} T_a}{T_b \times \sum_{i=1}^{n} C_a}\right) \times 100(\%) \quad \text{<Equation 1>}$$

wherein n is the number of examination after spraying, $C_b$ is a number of target pests per standard area of the non-sprayed field before spraying, $C_a$ is a number of target pests per standard area of the non-sprayed field after spraying, $T_b$ is a number of target pests per standard area of the sprayed field before spraying, and $T_a$ is a number of target pests per standard area of the sprayed field after spraying.

TABLE 1

| Formulation Example | Number of female adults of *Tetranychus uriticae*/pot | | | | Control value (%) |
|---|---|---|---|---|---|
| | Before spraying | 3 days after | 7 days after | 15 days after | |
| 2 | 223 | 9 | 8 | 25 | 97 |
| 3 | 254 | 0 | 0 | 54 | 97 |
| 4 | 276 | 3 | 1 | 7 | 99 |
| 6 | 321 | 0 | 1 | 41 | 98 |
| 7 | 298 | 0 | 3 | 33 | 98 |
| 13 | 221 | 0 | 1 | 29 | 98 |
| Mineral oil EC* | 255 | 2 | 1 | 7 | 99 |
| Non-treated field | 189 | 208 | 337 | 654 | — |

*emulsifiable concentrate containing mineral oil as an active ingredient

Test Example 2

Potency test against powdery mildew of strawberry

To powdery mildew which was spontaneously infestated on a strawberry (variety: Toyonoka) in a non-heated vinyl house, dilute solutions (dilution ratio: 50 or 100) of the compositions of the present invention shown in Formulation Example 1 as well as dilute solution (dilution ratio: 4000) of 10% microbutanyl wettable powder (Larry wettable powder, manufactured by Tokyo Organic Chemical Industries Co., Ltd.) and dilute solution (dilution ratio: 3000) of 30% trifumisol wettable powder (Trifumin wettable powder, manufactured by Nihon Soda Co., Ltd.) as controls were sprayed in a sufficient amount, using a hanging type sprayer. The severity of powdery mildew was examined about nine leaves per one stub, 7 days after spraying (one field/five stubs/two times). The severity and control value were calculated from the following equations.

$$\text{Severity} = \frac{\Sigma(\text{index} \times \text{number of corresponding leaves})}{4 \times \text{number of leaves examined}} \times 100$$

$$\text{Control value} = \frac{\text{severity of non-treated field} - \text{severity of treated field}}{\text{severity of non-treated field}} \times 100$$

The examination criteria (index) are shown below.

| Index | Severity (rate of lesion area) |
|---|---|
| 1 | less than 10% |
| 2 | 10 to less than 25% |
| 3 | 25 to less than 50% |
| 4 | not less than 50% |

The results are shown in Table 2. The average severity before treatment was 22.9. The composition of the present invention showed about the same control effect as that of 10% microbutanyl wettable powder or 30% trifumisol wettable powder.

TABLE 2

| Formulation Example | Dilution ratio | Seven days after spraying | Control value |
|---|---|---|---|
| 1 | ×50 | 17.8 | 55.2 |
| | ×100 | 21.4 | 46.1 |
| 10% Microbutanyl wettable powder | ×4000 | 14.5 | 63.5 |

TABLE 2-continued

| Formulation Example | Dilution ratio | Seven days after spraying | Control value |
|---|---|---|---|
| 30% Trifumisol wettable powder | ×3000 | 22.5 | 43.3 |
| Non-treated field | | 39.7 | — |

Test Example 3

About 20 female adults of *Panonychus citri* were put on a leaf of Japanese orange by which wet thin paper was surrounded. Then, each composition shown in the Formulation Examples 8 to 12 was diluted (dilution ratio: 100) with water and the dilution obtained was sprayed over the leaf in an amount of 4.8 mg/cm$^2$, and the leaf was left. After 48 hours, the numbers of survivors and deaths were examined and the control effect was calculated from the following equation. The test repeated three times.

Control effect (%) = $\frac{\text{Number of deaths}}{\text{Number of deaths + survivors}} \times 100$ <Equation 2>

The results are shown in Table 3.

TABLE 3

| Formulation Example | Control effect |
|---|---|
| 8 | 100 |
| 9 | 95 |
| 10 | 85 |
| 11 | 100 |
| 12 | 85 |

Test Example 4

The compositions were prepared according to the Formulation Example 9 and Comparative Formulation Example 1, and left. The former composition (Formulation Example 9) was liquid which was viscous and uniform. On the other hand, the latter composition (Comparative Formulation Example 1) was not uniform since components of the composition separated each other immediately.

What is claimed is:

1. A composition for controlling pests, comprising a starch obtained by α-isonerizing starch and at least one surfactant selected from the group consisting of dialkyl sulfosuccinate surfactants, silicone surfactants and acetylene glycol type surfactants.

2. The composition according to claim 1, wherein the amount of the starch obtained by α-isonerizing starch is 1.5 to 10% by weight and the amount of the surfactant is 1 to 8% by weight on the basis of the total weight of the composition.

3. The composition according to claim 1, further comprising a propylene glycol.

4. The composition according to claim 2, further comprising 5 to 20% by weight of a propylene glycol.

5. A composition for controlling pests, comprising a starch obtained by α-isonerizing starch and a silicone surfactant.

6. The composition according to claim 5, wherein the amount of the starch obtained by α-isonerizing starch is 1.5 to 10% by weight and the amount of the silicone surfactant is 1 to 8% by weight on the basis of the total weight of the composition.

7. A composition for controlling pests, comprising a starch obtained by α-isonerizing starch, a silicone surfactant and a propylene glycol.

8. The composition according to claim 7, wherein the amount of the starch obtained by α-isonerizing starch is 1.5 to 10% by weight, the amount of the silicone type surfactant is 1 to 8% by weight and the amount of the propylene glycol is 5 to 20% by weight on the basis of the total weight of the composition.

9. A method for controlling pests which comprises applying a pesticidally effective amount of a composition according to claims 1, 2, 3, 4, 5, 6, 7 or 8 to pests or plants in which pests live.

10. The method according to claim 9, wherein the composition is diluted with water and applied to make the concentration of starch obtained by α-isonerizing starch to 100 to 3000 ppm.

11. A composition according to claim 1, consisting essentially of a starch obtained by α-isomerizing starch and at least one surfactant selected from the group consisting of dialkyl sulfosufcinate surfactants, silicone surfactants and acetylene glycol surfactants.

* * * * *